US012673114B2

(12) United States Patent
Baek et al.

(10) Patent No.: US 12,673,114 B2
(45) Date of Patent: Jul. 7, 2026

(54) COMPOSITION FOR PREVENTING OR TREATING CANCER, CONTAINING IL-2 SURFACE EXPRESSION-EXTRACELLULAR VESICLES AS ACTIVE INGREDIENT

(71) Applicants:KYUNGPOOK NATIONAL UNIVERSITY INDUSTRY-ACADEMIC COOPERATION FOUNDATION, Daegu (KR); DAEGU GYEONGBUK INSTITUTE OF SCIENCE AND TECHNOLOGY, Daegu (KR)

(72) Inventors: Moon Chang Baek, Daegu (KR); Do Kyung Jung, Daegu (KR); Kyungmoo Yea, Daegu (KR)

(73) Assignees: KYUNGPOOK NATIONAL UNIVERSITY INDUSTRY-ACADEMIC COOPERATION FOUNDATION, Daegu (KR); DAEGU GYEONGBUK INSTITUTE OF SCIENCE AND TECHNOLOGY, Daegu (KR)

( * ) Notice: Subject to any disclaimer, the term of this patent is extended or adjusted under 35 U.S.C. 154(b) by 1052 days.

(21) Appl. No.: 17/621,234

(22) PCT Filed: Sep. 2, 2020

(86) PCT No.: PCT/KR2020/011774
§ 371 (c)(1),
(2) Date: Dec. 20, 2021

(87) PCT Pub. No.: WO2021/045501
PCT Pub. Date: Mar. 11, 2021

(65) Prior Publication Data
US 2022/0409741 A1 Dec. 29, 2022

(30) Foreign Application Priority Data

Sep. 2, 2019 (KR) ........................ 10-2019-0108284
Jul. 29, 2020 (KR) ........................ 10-2020-0094583

(51) Int. Cl.
| | |
|---|---|
| *A61K 47/69* | (2017.01) |
| *A61K 31/337* | (2006.01) |
| *A61K 31/475* | (2006.01) |
| *A61K 31/513* | (2006.01) |
| *A61K 33/243* | (2019.01) |
| *A61K 35/17* | (2015.01) |
| *A61K 38/12* | (2006.01) |
| *A61K 39/395* | (2006.01) |
| *A61K 47/64* | (2017.01) |
| *A61K 47/65* | (2017.01) |
| *A61P 35/00* | (2006.01) |

(52) U.S. Cl.
CPC ........ *A61K 47/6911* (2017.08); *A61K 31/337* (2013.01); *A61K 31/475* (2013.01); *A61K 31/513* (2013.01); *A61K 33/243* (2019.01);

*A61K 35/17* (2013.01); *A61K 38/12* (2013.01); *A61K 39/3955* (2013.01); *A61K 47/642* (2017.08); *A61K 47/6425* (2017.08); *A61K 47/65* (2017.08); *A61P 35/00* (2018.01)

(58) Field of Classification Search
None
See application file for complete search history.

(56) References Cited

U.S. PATENT DOCUMENTS

| | | | |
|---|---|---|---|
| 2018/0117117 A1 | 5/2018 | Choi et al. | |
| 2018/0177727 A1 | 6/2018 | Kalluri et al. | |
| 2020/0148746 A1 | 5/2020 | Koh et al. | |

(Continued)

FOREIGN PATENT DOCUMENTS

| | | |
|---|---|---|
| KR | 10-2016-0130949 A | 11/2016 |
| KR | 10-2018-0017119 A | 2/2018 |
| KR | 10-2018-0078173 A | 7/2018 |

(Continued)

OTHER PUBLICATIONS https://www.mayoclinic.org/diseases-conditions/glioblastoma/symptoms-causes/syc-20569077#:~:text=There's%20no%20cure%20for%20glioblastoma.%20Treatments%20might%20slow%20cancer%20growth%20and%20reduce%20symptoms. (Year: 2025).*

(Continued)

*Primary Examiner* — Anand U Desai
*Assistant Examiner* — Catheryne Chen
(74) *Attorney, Agent, or Firm* — Revolution IP, PLLC

(57) ABSTRACT

The present invention relates to a composition for preventing or treating cancer, the composition containing IL-2 surface expression-extracellular vesicles as an active ingredient. According to the present invention, immune cells, in which useful cytokines have been expressed on the cell surface, and extracellular vesicles, preferably small extracellular vesicles (sEV), which are derived from the immune cells and have useful cytokines expressed on the surface were prepared using a lentiviral vector containing a cytokine-linker-a PDGF receptor transmembrane domain, and it was found that the extracellular vesicles increased proliferation and activity of cytotoxic T cells thereby increasing anti-cancer immune efficacy. Thus, the extracellular vesicles having the efficacy can be usefully utilized as a pharmaceutical composition for preventing or treating cancer, a pharmaceutical composition for co-administration with an anti-cancer drug, or a composition for delivering a drug or a physiologically active material.

3 Claims, 15 Drawing Sheets

Specification includes a Sequence Listing.

(56)         References Cited

U.S. PATENT DOCUMENTS

2020/0206360 A1     7/2020   Choi et al.

FOREIGN PATENT DOCUMENTS

| | | | |
|---|---|---|---|
| KR | 10-2019-0019872 A | 2/2019 | |
| WO | 03/016522 A2 | 2/2003 | |
| WO | 2017/173367 A2 | 10/2017 | |
| WO | WO-2018161026 A1 * | 9/2018 | ......... A61K 38/1793 |
| WO | 2019-027847 A1 | 2/2019 | |

OTHER PUBLICATIONS 2023, https://www.cancerresearchuk.org/about-cancer/what-is-cancer/genes-dna-and-cancer (Year: 2023).*

2023, https://www.cancerresearchuk.org/about-cancer/what-is-cancer/how-cancer-starts/types-of-cancer (Year: 2023).*

2023, https://www.cancerresearchuk.org/about-cancer/what-is-cancer/understanding-cancer-statistics-incidence-survival-mortality (Year: 2023).*

Cheng et al., Reprogramming Exosomes as Nanoscale Controller of Cellular immunity, 2018, J Am Chem Soc, 140: 16413-16417.*

Spolski et al., Biology and regulation of IL-2: from molecular mechanisms to human therapy, 2018, Nature, 18: 648-659.*

International Search Report for PCT/KR2020/011774 mailed Dec. 17, 2020 from Korean Intellectual Property Office.

Yang, Yunshan et al., "Increased induction of antitumor response by exosomes derived from interleukin-2 gene-modified tumor cells", Journal of Cancer Research and Clinical Oncology, 2007, vol. 133, pp. 389-399.

Fitzgerald, Wendy et al., "A System of Cytokines Encapsulated in ExtraCellular Vesicles", Scientific Report, 2018, vol. 8, Article No. 8973.

S. H. Kim et al., "Effective Treatment of Inflammatory Disease Models with Exosomes Derived from Dendritic Cells Genetically Modified to Express IL-4", The Journal of Immunology, vol. 179, No. 4, 2007, pp. 2242-2249.

Daniele Bellavia et al., "Interleukin 3-receptor targeted exosomes inhibit in vitro and in vivo Chronic Myelogenous Leukemia cell growth", Theranostics, vol. 7, No. 5, Mar. 16, 2017, pp. 1333-1345.

The extended European Search Report of European Application No. 20861461 mailed Jun. 9, 2023.

Tao Jiang et al., "Role of IL-2 in cancer immunotherapy", Oncoimmunology, 2016, vol. 5, No. 6, e1163462 (10 pages).

* cited by examiner

[FIG. 1]
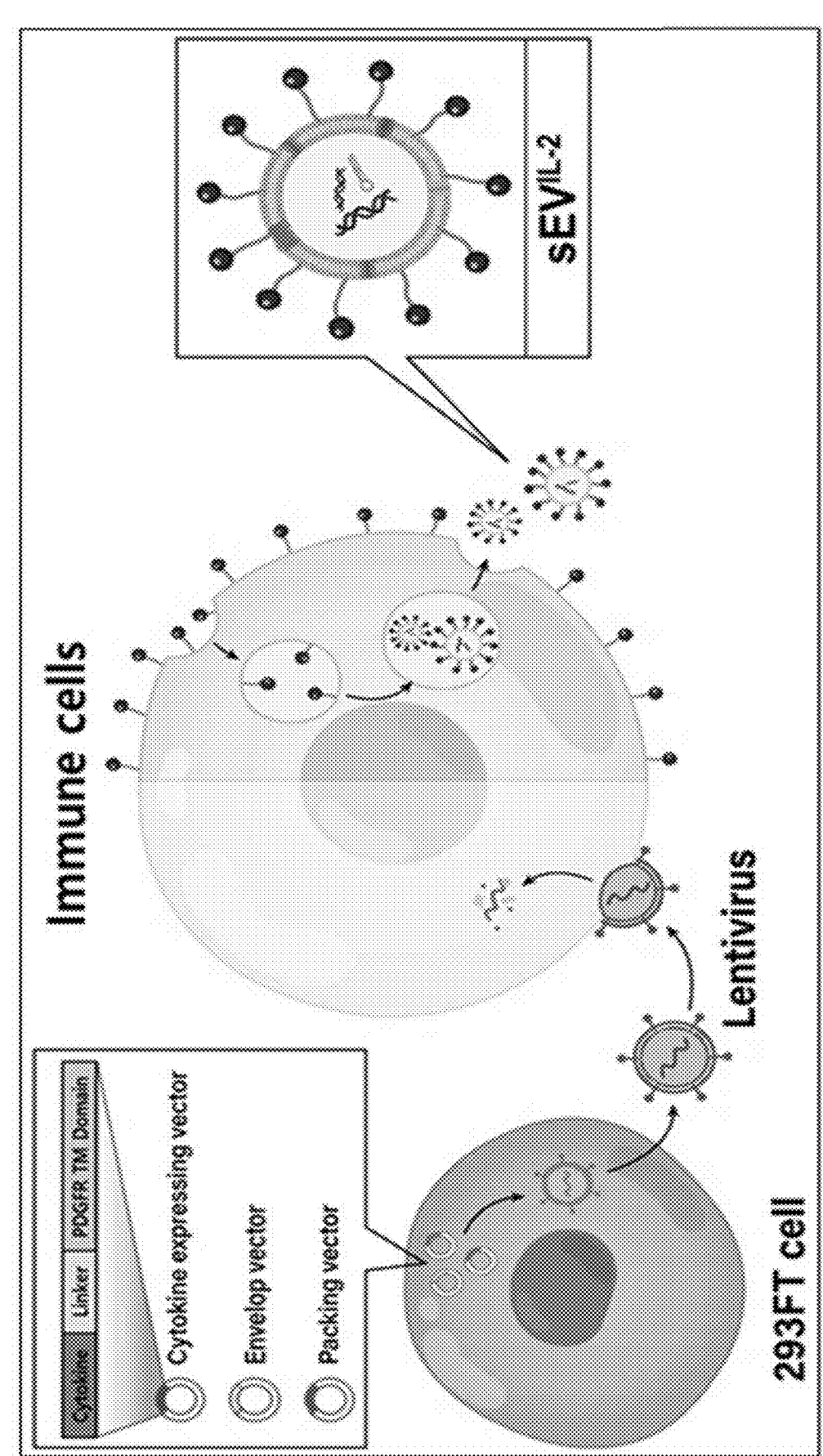

[FIG. 2]
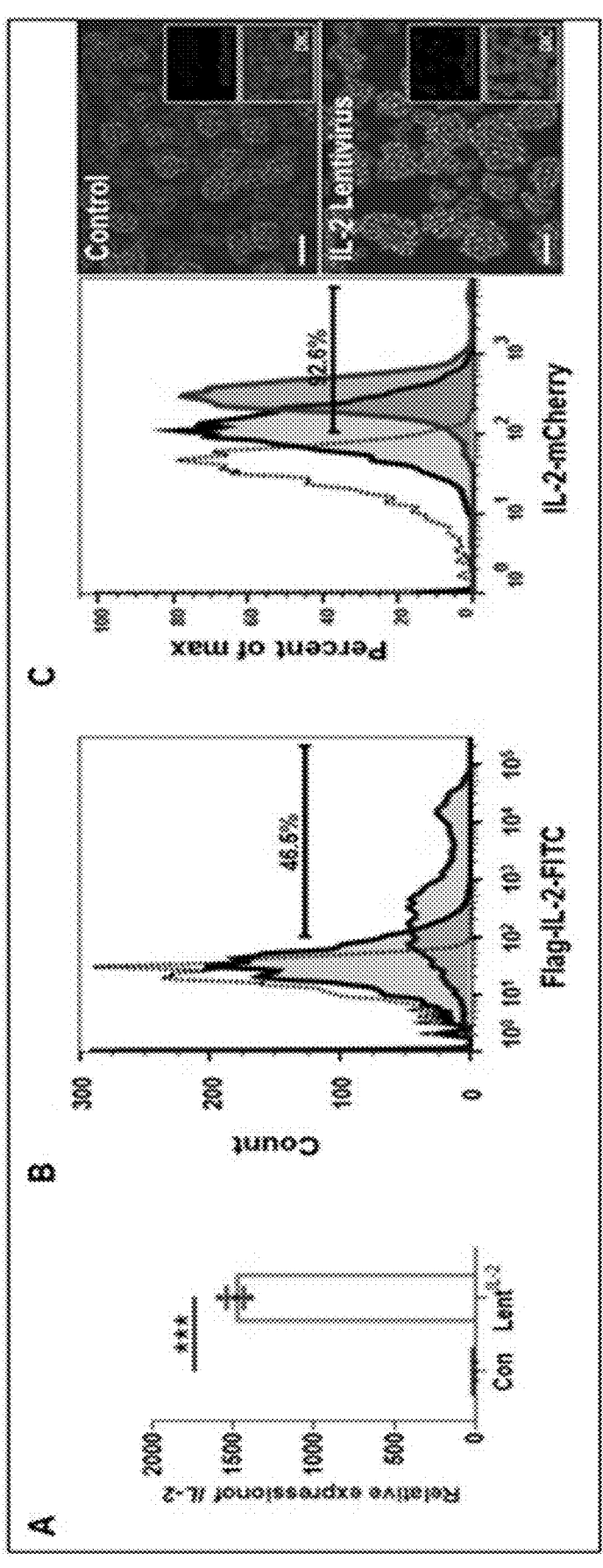

[FIG. 3]
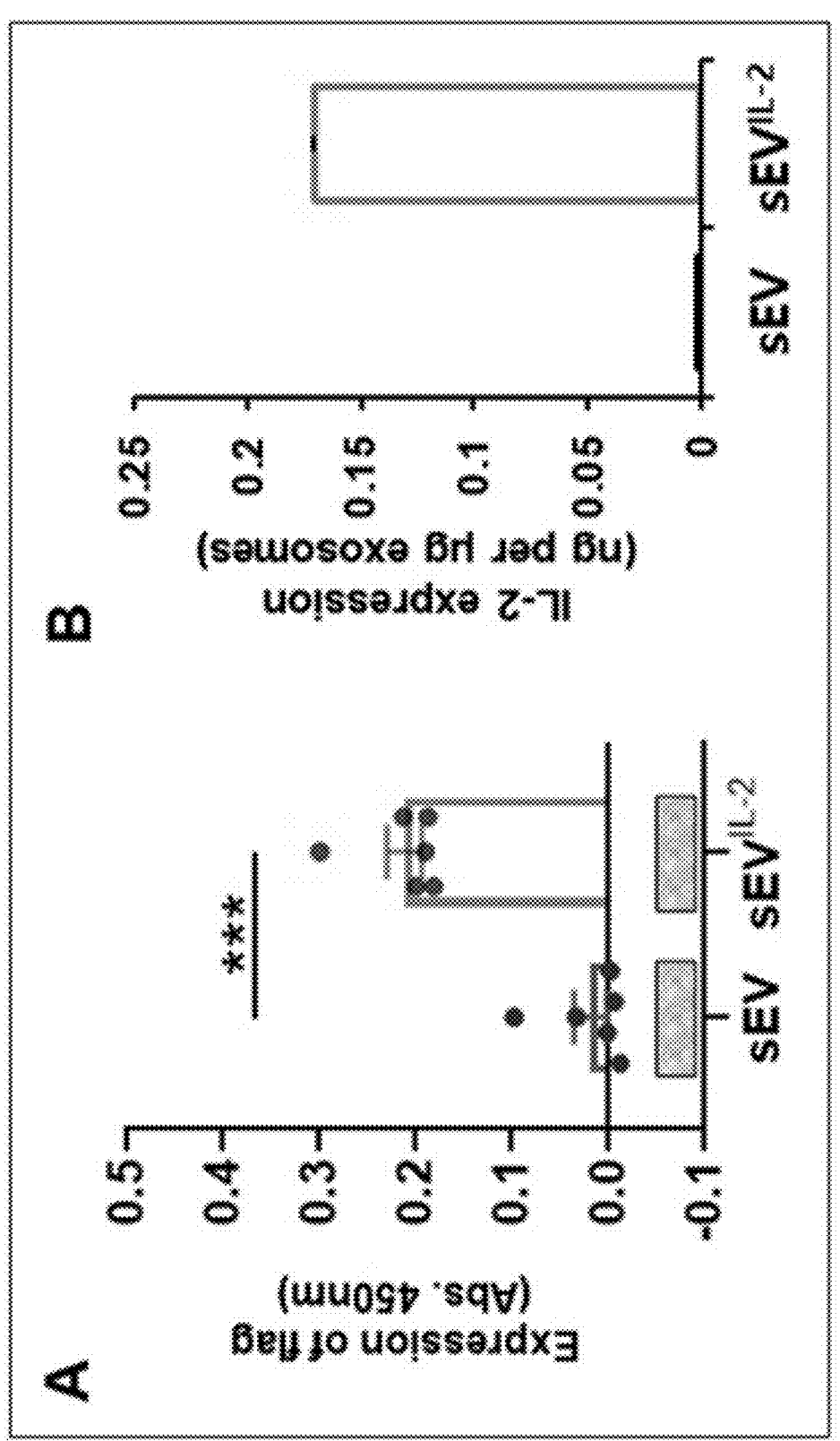

[FIG. 4]
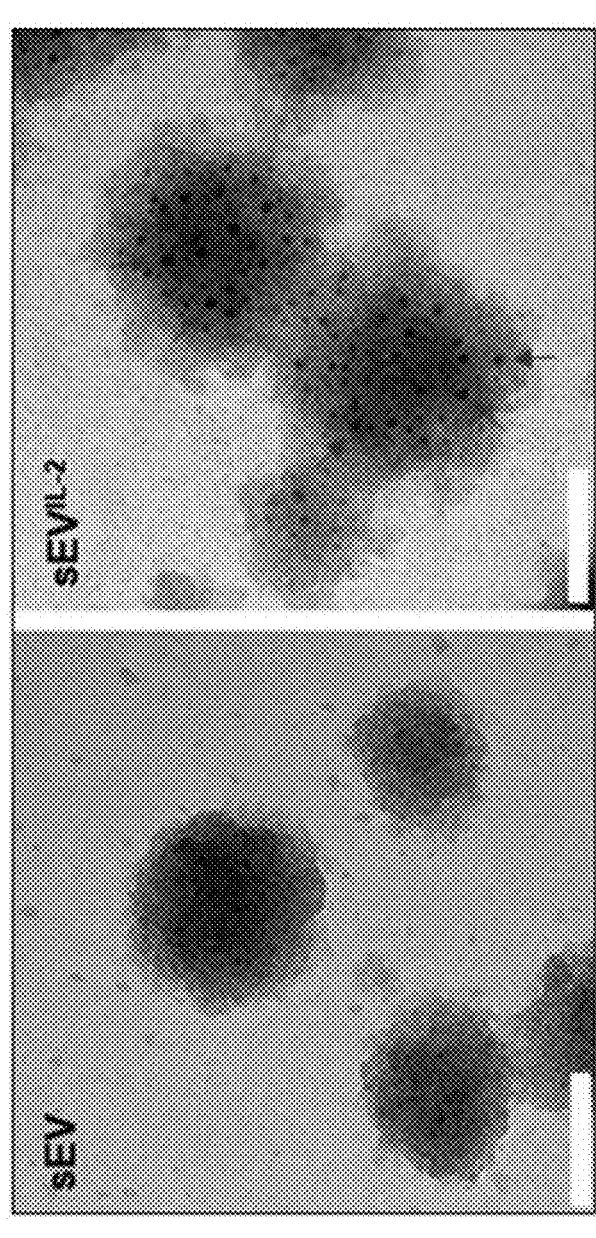

[FIG. 5]
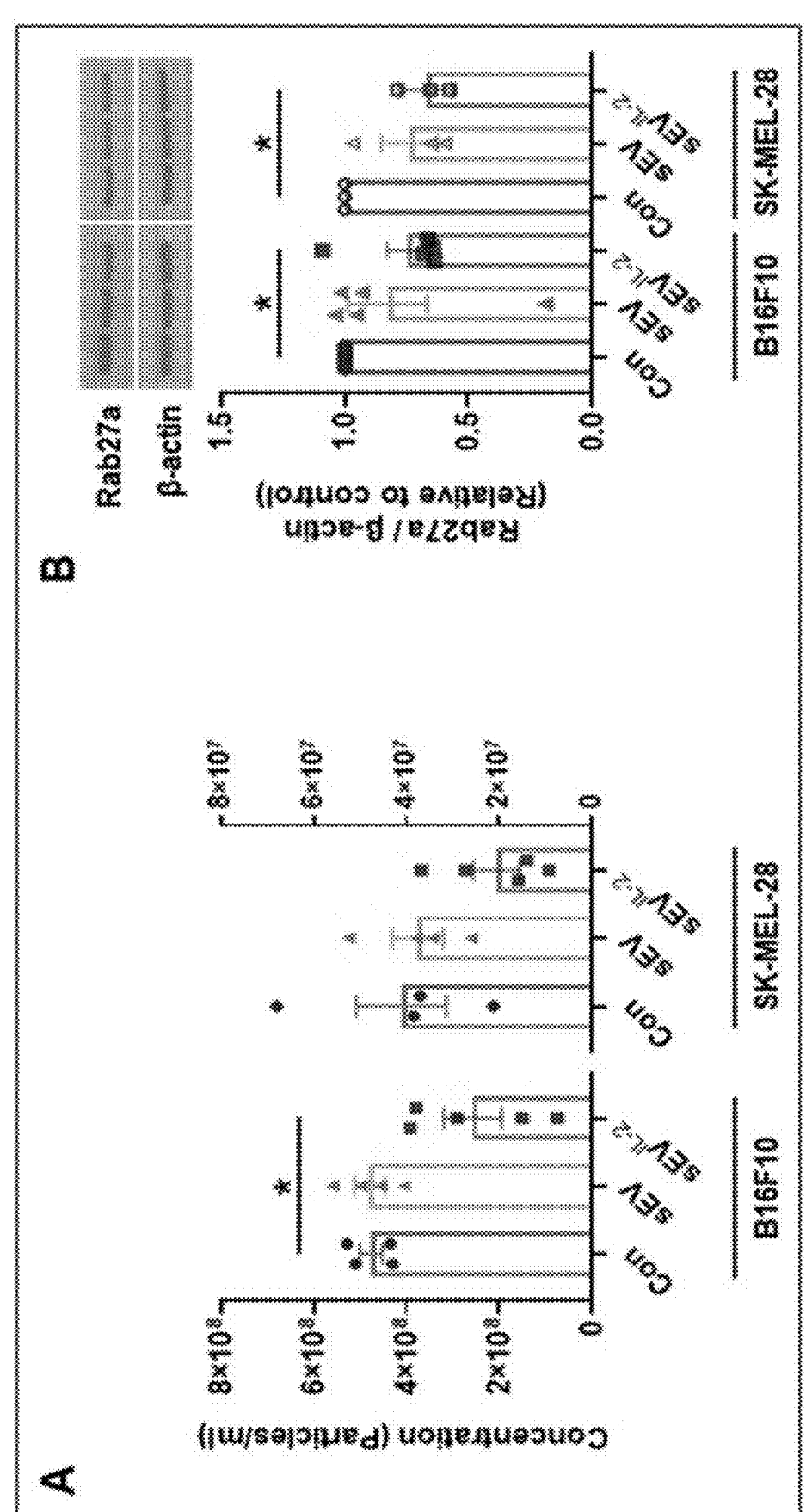

[FIG. 6]
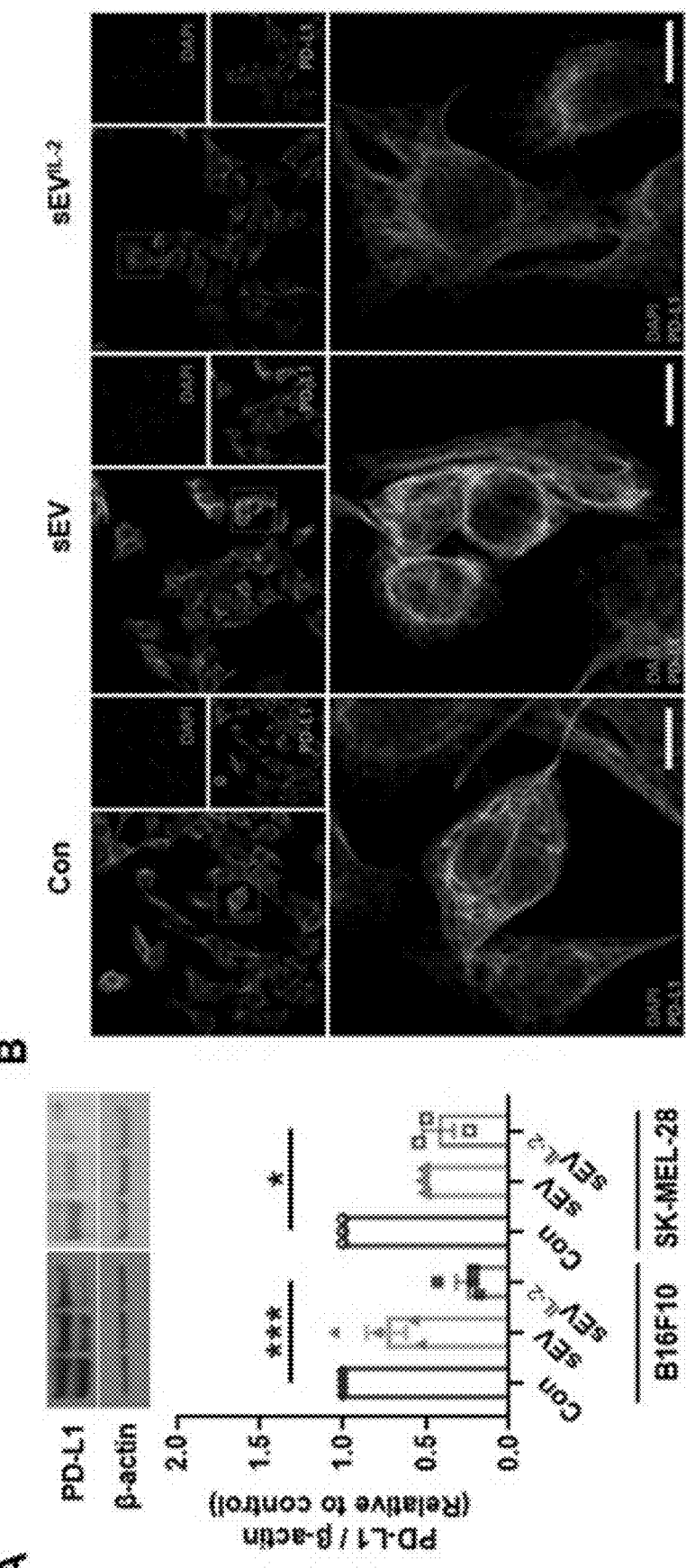

[FIG. 7]
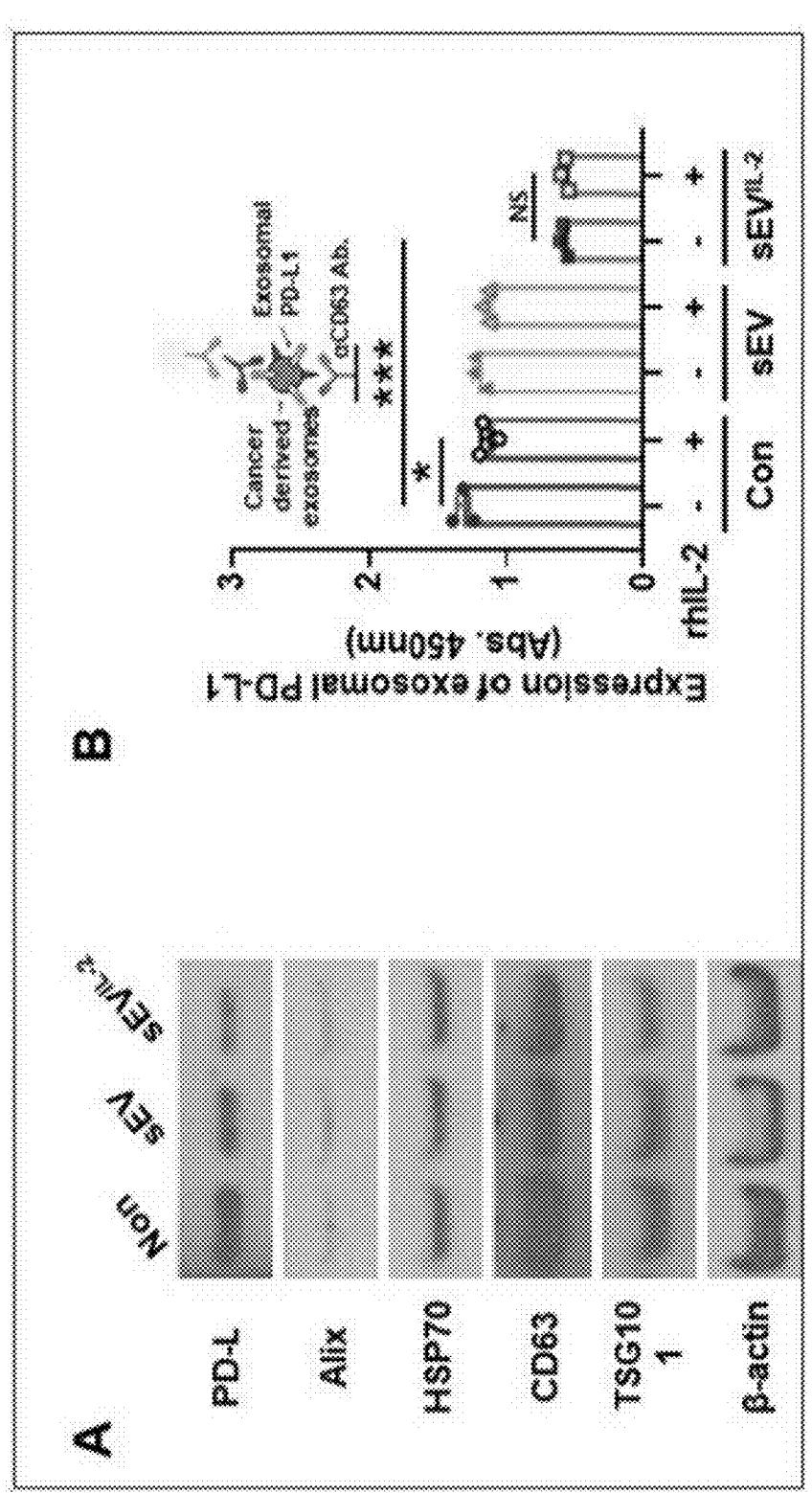

[FIG. 8]
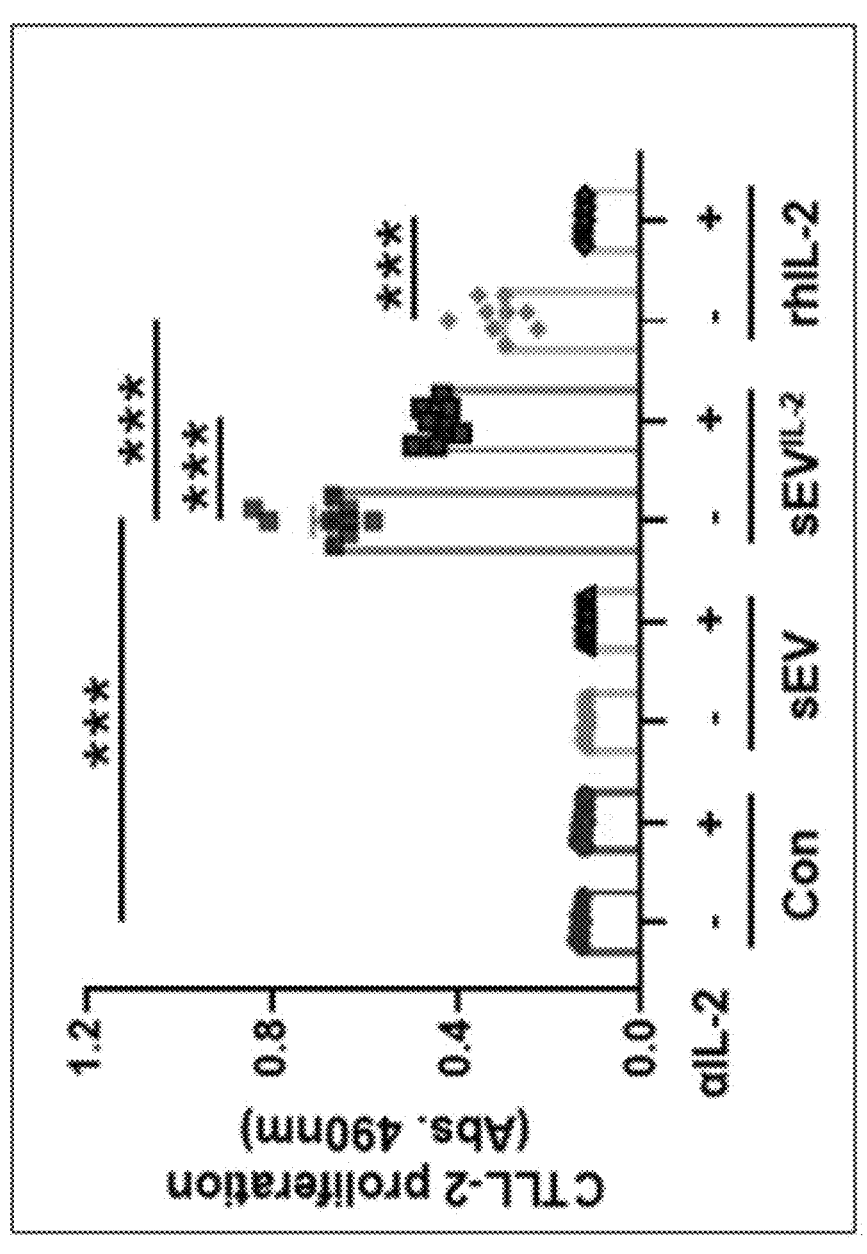

[FIG. 9]
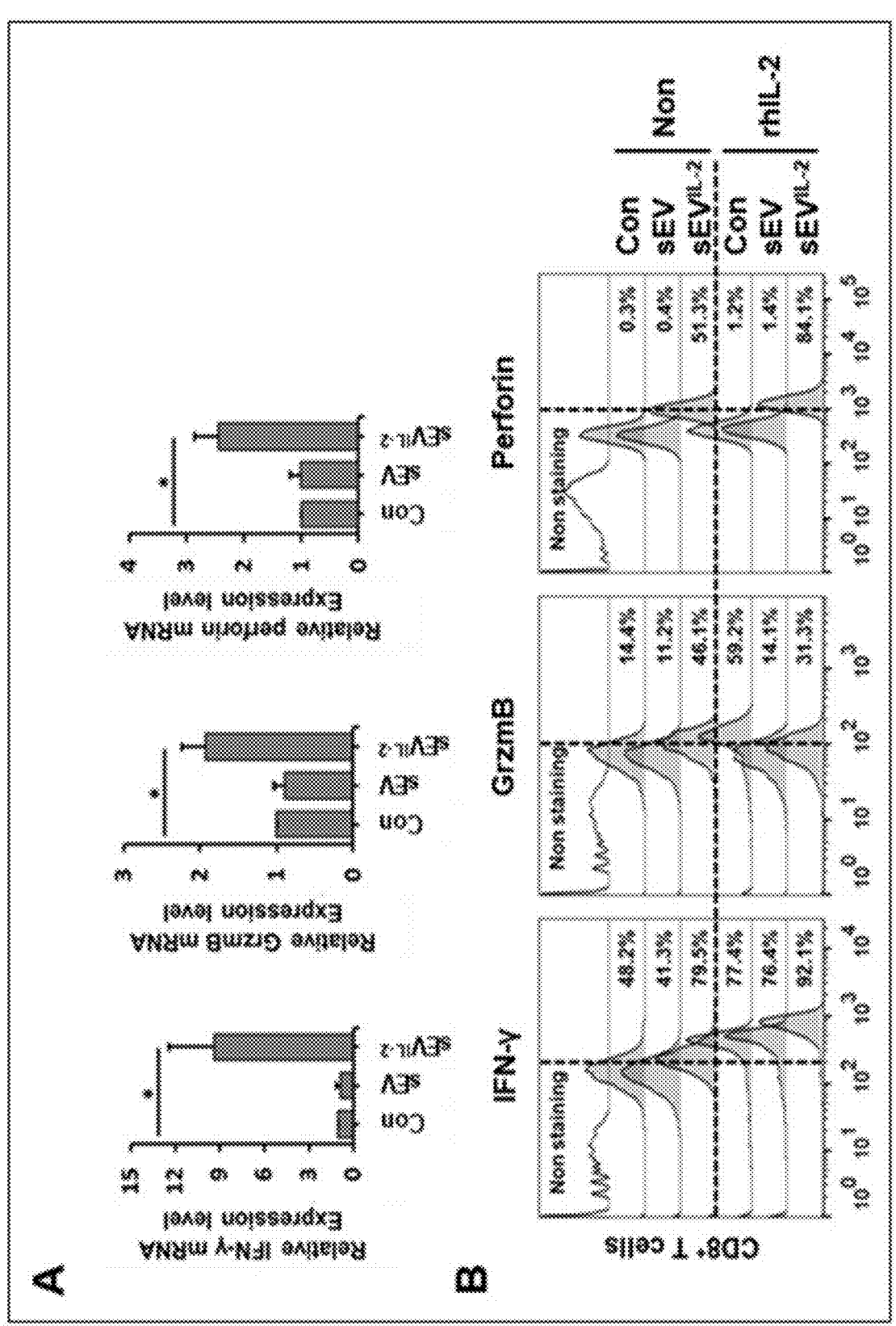

[FIG. 10]
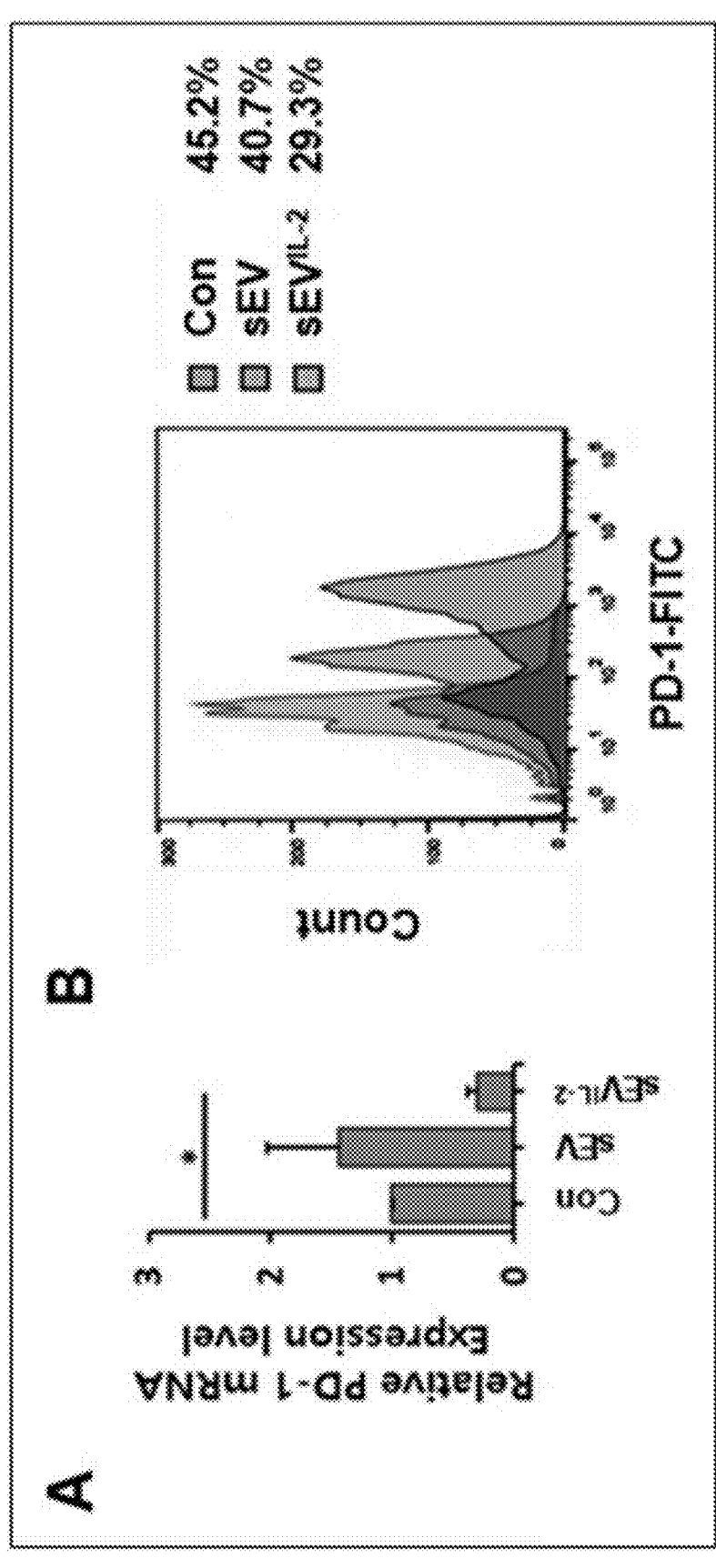

[FIG. 11]
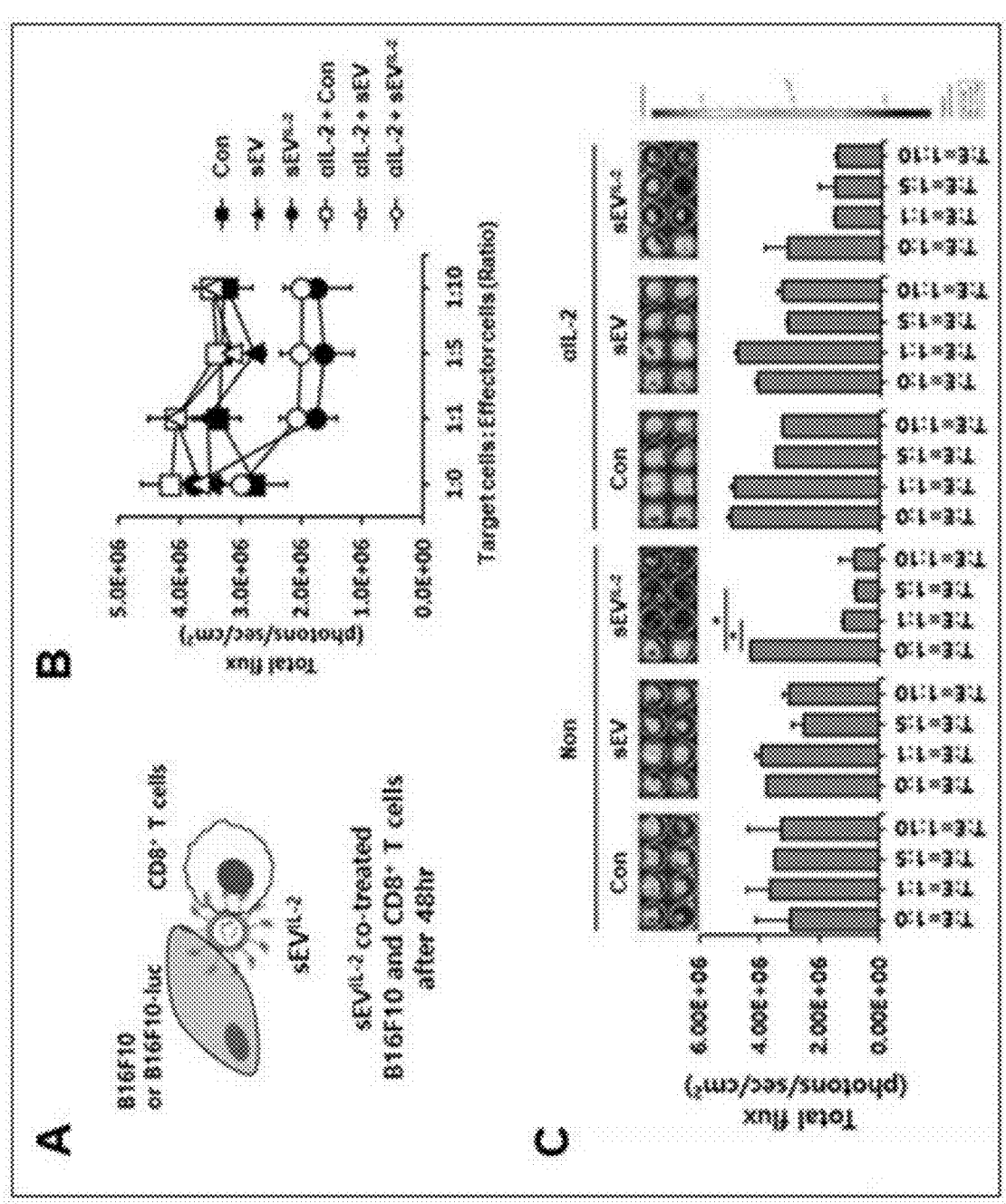

[FIG. 12]
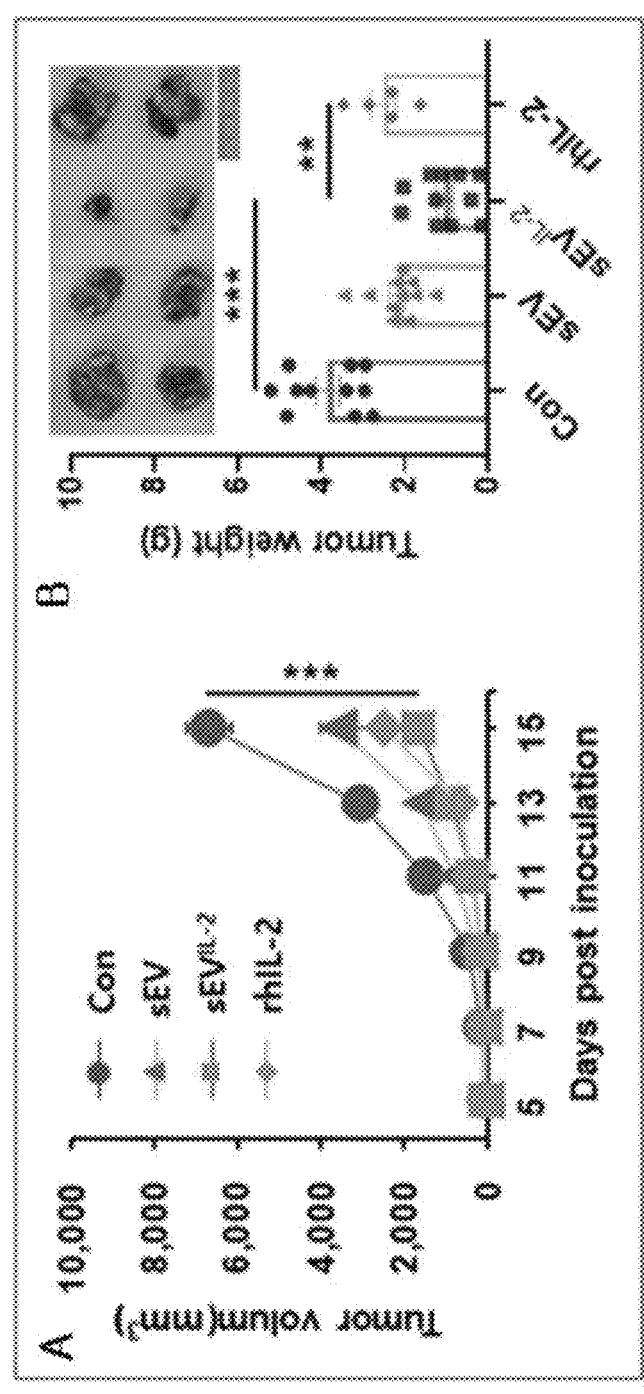

[FIG. 13]
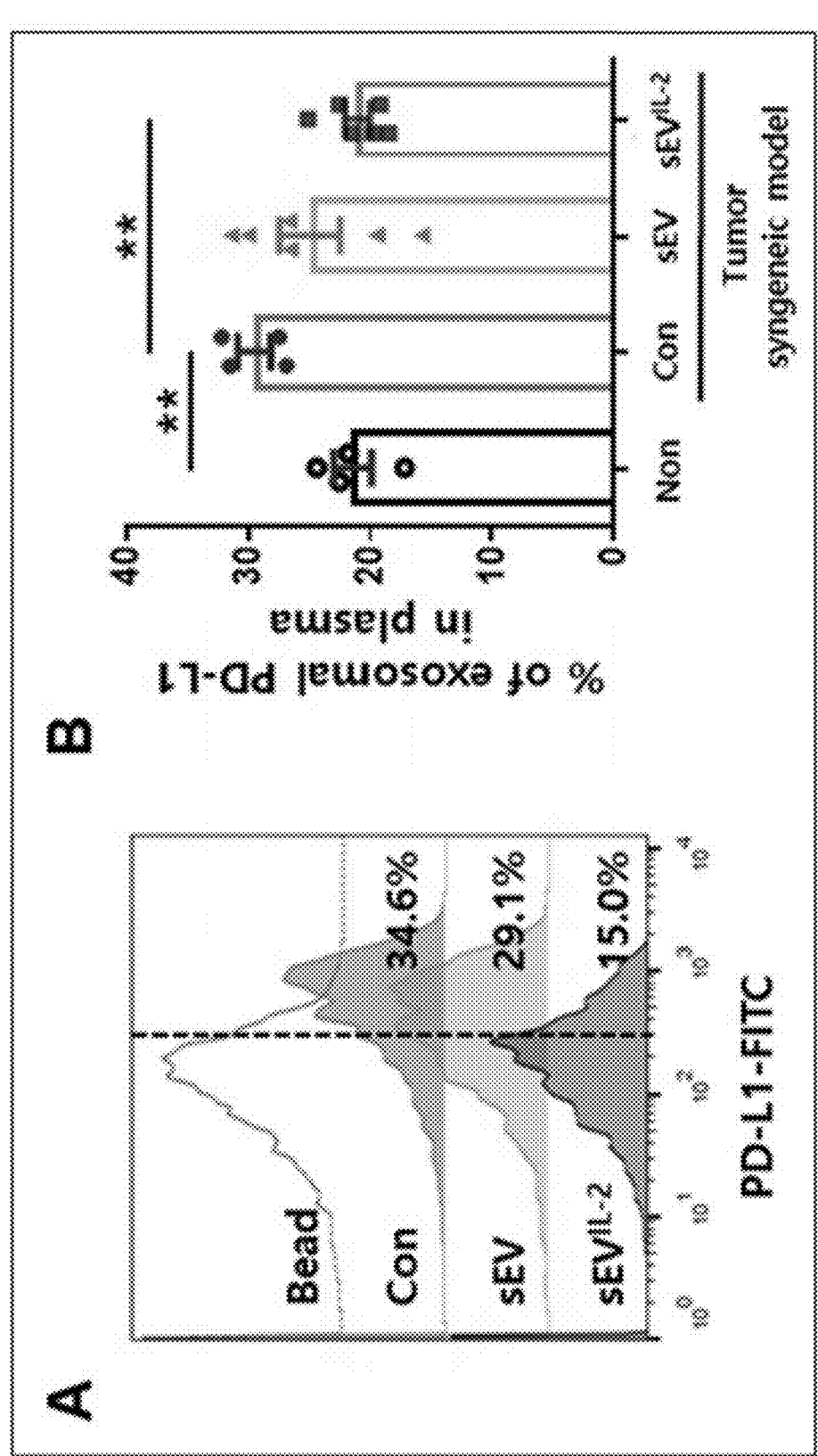

[FIG. 14]
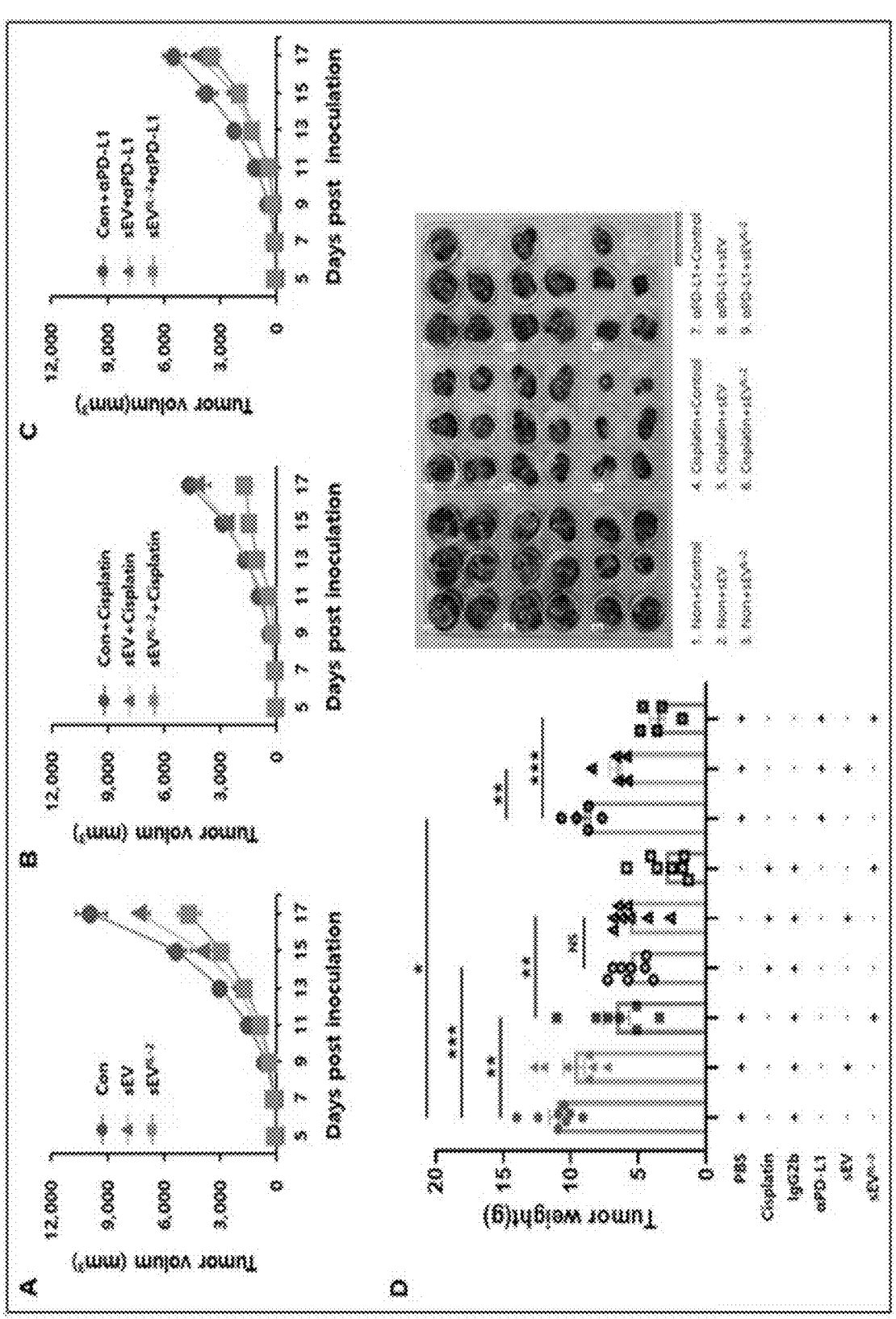

[FIG. 15]
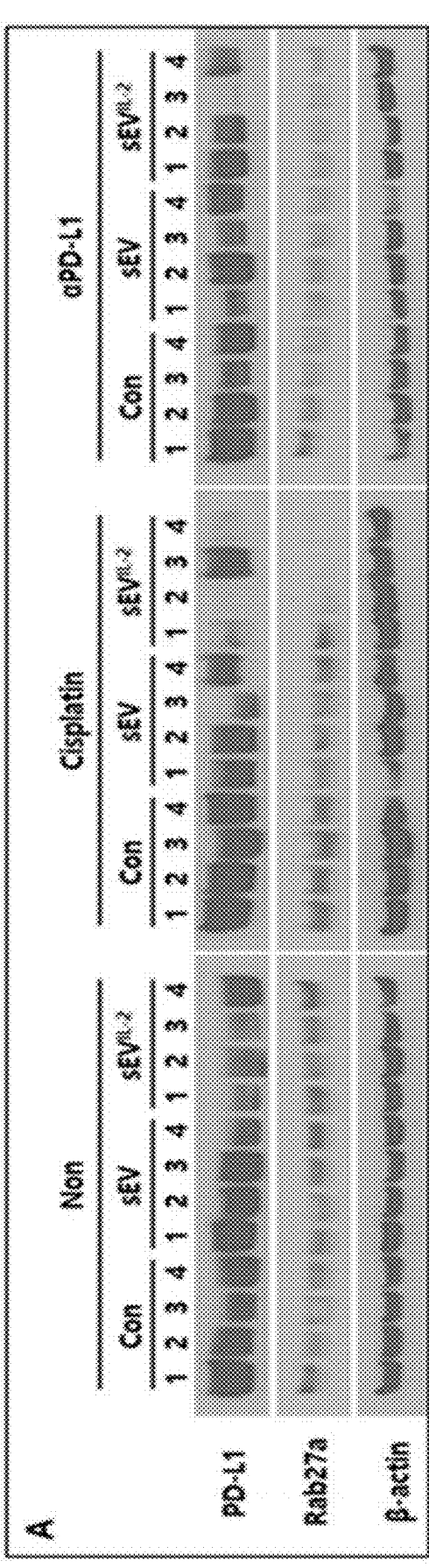

COMPOSITION FOR PREVENTING OR TREATING CANCER, CONTAINING IL-2 SURFACE EXPRESSION-EXTRACELLULAR VESICLES AS ACTIVE INGREDIENT

CROSS REFERENCE TO PRIOR APPLICATIONS

This application is a National Stage Application of PCT International Patent Application No. PCT/KR2020/011774 filed on Sep. 2, 2020, under 35 U.S.C. § 371, which claims priority to Korean Patent Application Nos. 10-2019-0108284 filed on Sep. 2, 2019 and 10-2020-0094583 filed on Jul. 29, 2020, respectively, which are all hereby incorporated by reference in their entirety.

TECHNICAL FIELD

The present invention relates to a composition for preventing or treating cancer, containing IL-2 surface expression-extracellular vesicles as an active ingredient.

BACKGROUND ART

Small extracellular vesicles (sEVs) are small membrane vesicles secreted from most cells. The diameter of sEV is approximately 30-100 nm, and sEV contains various types of proteins, genetic materials (DNA, RNA, miRNA), lipids, and the like, originating from the cell. sEV is released and secreted out of the cell, originating in specific intracellular compartments called multivesicular bodies (MVBs), rather than directly detaching from plasma membrane. In other words, when fusion of the multivesicular bodies and the plasma membrane occurs, vesicles are released into the extracellular environment, which is called sEV. Although it has not been identified exactly by what mechanism sEV is made, it is known that sEV is isolated and released from various cell types under both normal and pathological conditions.

Cancer is a result of uncontrolled and disordered cell proliferation caused by an abnormal excess of cells. From a molecular biological point of view, cancer is a disease caused by genetic mutation. There are dozens of types of cancer that have been identified so far, and they are mainly classified according to the location of the diseased tissue. Cancer is divided into benign and malignant tumors. Benign tumors grow relatively slowly and do not metastasize from their primary site to other tissues, whereas malignant tumors leave their primary site, invade other tissues, and grow rapidly, and are life-threatening due to this characteristic. Most cancers are asymptomatic in the early stages, and even if there are symptoms, they are mild, so most people tend to overlook them, which increases the cancer death rate.

Surgical therapy, chemotherapy, radiation therapy, and the like, are used for treatment of cancer, but it is reported that more than 50% of all cancer patients eventually die without being cured despite many studies. The reason is that cancer recurs because microscopically metastasized cancer cells are not removed even after surgical resection, death of cancer cells is not induced by an anticancer drug, or cancer cells that have developed resistance to the anticancer drug rapidly increase during or after the treatment although tumor appears to be shrinking due to a response to the anticancer drug at the initial stage. Today, about 60 types of various anticancer drugs are being used, and researches on the development of new anticancer drugs are being actively conducted as knowledge about cancer occurrence and characteristics of cancer cells is widely known. However, most anticancer drugs cause serious side effects such as nausea and vomiting, hair loss, skin and nail discoloration, and nervous system side effects, and have a disadvantage of losing their therapeutic effects because the cancer cells acquire resistance to the anticancer drugs when repeatedly administered for a long period of time or when cancer recurs. Further, the radiation therapy induces the death of cancer cells by irradiating high-energy radiation to the cancer tissue, but has a disadvantage of damaging normal tissues around the cancer tissue to cause side effects.

Therefore, development of multi-function immune sEVs in which useful cytokines are expressed from immune cells using cytokines specific for cancer treatment has the advantage of maximizing cancer prevention and treatment efficacy.

DISCLOSURE

Technical Problem

It is an object of the present invention to provide cytokine surface expression-extracellular vesicles.

Another object of the present invention is to provide a pharmaceutical composition for preventing or treating cancer containing the extracellular vesicles as an active ingredient.

Another object of the present invention is to provide a pharmaceutical composition containing the extracellular vesicles as an active ingredient for co-administration of an anticancer drug.

Another object of the present invention is to provide a composition for delivery of a drug or a physiologically active substance.

Technical Solution

In order to achieve the above objects, the present invention provides an extracellular vesicle in which a cytokine; linker; and a transmembrane protein are fused.

Further, the present invention provides a pharmaceutical composition for preventing or treating cancer containing the extracellular vesicle as an active ingredient.

Further, the present invention provides a pharmaceutical composition for preventing or treating cancer containing the extracellular vesicle and an anticancer drug as active ingredients.

Furthermore, the present invention provides a composition for delivery of a drug or a physiologically active substance, containing one or more of a drug and a physiologically active substance, and an extracellular vesicle in which a cytokine; linker; and a transmembrane protein are fused, wherein the drug or physiologically active substance is encapsulated in a lipid layer of the extracellular vesicle.

Advantageous Effects

According to the present invention, using a lentiviral vector containing a cytokine-linker-a PDGF receptor transmembrane domain, immune cells with useful cytokines expressed on the cell surface, and extracellular vesicles derived from the immune cells and with useful cytokines expressed on the surface, preferably small extracellular vesicles (sEV) were prepared. It was determined that the extracellular vesicles increased proliferation and activity of cytotoxic T cells to increase an immune anticancer effect. Extracellular vesicles having the effect can be usefully utilized as a pharmaceutical composition for preventing or treating cancer, a pharmaceutical composition for co-administration of anticancer drugs, and a composition for delivering drugs or physiologically active substances.

BRIEF DESCRIPTIONS OF DRAWINGS

FIG. 1 shows a structure of a lentiviral vector containing a cytokine-linker-a PDGF receptor transmembrane domain and a method for preparing multi-function immune small extracellular vesicles (sEVs).

FIG. 2 shows results of determining the expression level of IL-2 by performing a real-time polymerase chain reaction and flow cytometry for IL-2 surface expression Jurkat cells.

FIG. 3 shows results of determining the expression level of IL-2 by performing Western blot and ELISA analysis for IL-2 surface expression Jurkat cell-derived sEV (sEV$^{IL-2}$).

FIG. 4 shows an image of sEV$^{IL-2}$ obtained by transmission electron microscopy using a immunogold labeling method.

FIG. 5 shows results of determining decreases in the number of sEV and expression of Rab 27a by sEV$^{IL-2}$ in melanoma cells.

FIG. 6 shows results of determining a decrease in expression of PD-L1 by sEV$^{IL-2}$ in the melanoma cells.

FIG. 7 shows results of determining a decrease in expression of exosomal PD-L1 by sEV$^{IL-2}$ in the melanoma cells.

FIG. 8 shows a result of determining cell proliferation by sEV$^{IL-2}$ in cytotoxic T cells.

FIG. 9 shows results of determining T cell activity by sEV$^{IL-2}$ in the cytotoxic T cells.

FIG. 10 shows results of determining a decrease in PD-1 expression by sEV$^{IL-2}$ in the cytotoxic T cells.

FIG. 11 shows results of confirming apoptosis of melanoma cells in co-culture of the cytotoxic T cells and the melanoma cells treated with sEV$^{IL-2}$.

FIG. 12 shows results of confirming anticancer effects of sEV$^{IL-2}$ in a melanoma transplanted mouse model.

FIG. 13 shows results of confirming inhibitory effects of cancer cell-derived exosomal PD-L1 by sEV$^{IL-2}$ in melanoma transplanted mice.

FIG. 14 shows results of confirming anticancer effects of using a combination therapy of sEV$^{IL-2}$ and cisplatin or an anti-PD-L1 antibody in the melanoma transplanted mouse model.

FIG. 15 shows a result of confirming anticancer effects of using the combination therapy of sEV$^{IL-2}$ and cisplatin or the anti-PD-L1 antibody in the melanoma transplanted mouse model by Western blot.

BEST MODE

A membrane bound cytokine (MBC) platform consists of "a cytokine-linker-a transmembrane domain of platelet-derived growth factor (PDGF) receptor". The cytokine is linked to the transmembrane domain of the PDGF receptor through a flexible linker, and is expressed in a form attached to the cell membrane without being secreted to the outside of the cell.

In the present invention, as shown in FIG. 1, by applying the MBC platform to immune cells, immune cells having specific cytokines expressed on the surface of their cell membrane are prepared, and "immune cells-derived small extracellular vesicles (sEVs) having specific cytokines expressed on their surface" which are called avatars thereof were prepared and their efficacy was evaluated.

Accordingly, the present invention provides extracellular vesicles, wherein a cytokine; linker; and a transmembrane protein are fused in each of the extracellular vesicles.

The cytokine is bound to linker coupled to the transmembrane protein penetrating a lipid layer of the extracellular vesicle and is exposed on the surface of the extracellular vesicle.

The extracellular vesicles may be secreted from a cell transfected with a viral vector containing a cytokine; linker; and a transmembrane domain.

It is clear that the cytokine may be IL-2, but is not limited thereto.

The linker consists of an amino acid sequence represented by the general formula (GGGGS)n (SEQ ID NO: 1), (SGGGG)n (SEQ ID NO: 2), (SRSSG)n (SEQ ID NO: 3), (SGSSC)n (SEQ ID NO: 4), (GKSSGSGSESKS)n (SEQ ID NO: 5), (RPPPPC)n (SEQ ID NO: 6), (SSPPPPC) n NO: 7), (GSTSGSGKSSEGKG)n (SEQ ID NO: 8), (GST-SGSGKSSEGSGSTKG)n (SEQ ID NO: 9), (GST-SGSGKPGSGEGSTKG)n (SEQ ID NO: 10), or (EGKSSGSGSESKEF)n (SEQ ID NO: 11), wherein n may be an integer from 1 to 20.

The transmembrane domain may be a transmembrane domain of one or more receptors selected from the group consisting of epidermal growth factor receptor, insulin receptor, platelet-derived growth factor (PDGF) receptor, vascular endothelial growth factor receptor, fibroblast growth factor receptor, cholecystokinin (CCK) receptor, neurotrophic factor (NGF) receptor, hepatocyte growth factor (HGF) receptor, Ephrin (Eph) receptor, angiopoietin receptor, and RTK (Related to receptor tyrosine kinase) receptor, but it should be noted that the present invention is not limited thereto.

The cell is a T cell, and more specifically, may be a helper T cell, but is not limited thereto.

The extracellular vesicles can increase anticancer effects by increasing proliferation and activity of cytotoxic T cells.

The extracellular vesicles are small extracellular vesicles (sEV) having a diameter of 30 to 100 nm, and may include exosomes and microvesicles, but it should be noted that the present invention is not limited thereto.

In addition, the present invention provides a pharmaceutical composition for preventing or treating cancer containing the extracellular vesicles as an active ingredient.

The cancer may be any one selected from the group consisting of melanoma, colon cancer, lung cancer, skin cancer, non-small cell lung cancer, colon cancer, bone cancer, pancreatic cancer, head or neck cancer, uterine cancer, ovarian cancer, rectal cancer, stomach cancer, perianal cancer, breast cancer, fallopian tube carcinoma, endometrial carcinoma, cervical carcinoma, vaginal carcinoma, vulvar carcinoma, Hawkins' disease, esophageal cancer, small intestine cancer, endocrine cancer, thyroid cancer, parathyroid cancer, adrenal cancer, soft tissue sarcoma, urethral cancer, penile cancer, prostate cancer, chronic or acute leukemia, lymphocytic lymphoma, bladder cancer, kidney or ureter cancer, renal cell carcinoma, renal pelvic carcinoma, central nervous system tumor, primary central nervous system lymphoma, spinal cord tumor, brainstem glioma, and pituitary adenoma, but it should be noted that the present invention is not limited thereto.

The pharmaceutical composition may be co-administered with an anticancer drug or an antibody, but it should be noted that the present invention is not limited thereto.

In addition, the present invention provides a pharmaceutical composition for preventing or treating cancer containing the extracellular vesicles and an anticancer drug as active ingredients, in other words, a pharmaceutical composition for co-administration with an anticancer drug for preventing or treating cancer.

The anticancer drug may be at least one selected from the group consisting of cisplatin, vinblastine, vincristine, actinomycin-D, 5-fluouracil, docetaxel, cabazitaxel, paclitaxel, and pembrolizumab, but it should be noted that the present invention is not limited thereto.

The pharmaceutical composition may be co-administered with the anticancer drug to increase the therapeutic effects on cancer.

For administration, the pharmaceutical composition of the present invention may include a pharmaceutically acceptable carrier, excipient, or diluent in addition to the active ingredients described above. The carrier, excipient, and diluent may include lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinylpyrrolidone, water, methylhydroxybenzoate, propylhydroxybenzoate, talc, magnesium stearate, and mineral oil.

The pharmaceutical composition of the present invention may be formulated and used in an oral dosage form such as powders, granules, tablets, capsules, suspensions, emulsions, syrups, or aerosols, or in the form of external preparations, suppositories, or sterile injection solutions, according to conventional methods, respectively. Specifically, when formulating, the diluent or excipient may be used such as a filler, a bulking agent, a binder, a wetting agent, a disintegrant, and a surfactant commonly used. Solid preparations for oral administration include, but are not limited to, tablets, pills, powders, granules, and capsules. Such a solid preparation may be prepared by mixing one or more excipients, for example, starch, calcium carbonate, sucrose, lactose, and gelatin, in addition to the active ingredient. In addition to simple excipients, lubricants such as magnesium stearate and talc may also be used. It may be prepared by adding various excipients, for example, wetting agents, sweetening agents, fragrances, and preservatives, in addition to liquids for oral use and liquid paraffin. Formulations for parenteral administration include sterile aqueous solutions, non-aqueous solvents, suspensions, emulsions, lyophilized formulations, and suppositories. As the non-aqueous solvent and suspension, propylene glycol, polyethylene glycol, vegetable oil such as olive oil, and injectable esters such as ethyl oleate may be used. As the base of the suppository, Witepsol, Macrosol, Tween 61, cacao butter, laurin fat, glycerogelatin, and the like, may be used.

A suitable dosage of the pharmaceutical composition of the present invention varies depending on the patient's condition and weight, the degree of disease, drug form, and time, but may be appropriately selected by those skilled in the art. The daily dosage of the composition is preferably 0.001 mg/kg to 50 mg/kg, and may be administered once a day or divided into several times a day as needed.

In addition, the present invention provides a composition for delivery of a drug or a physiologically active substance, containing one or more of a drug or a physiologically active substance, and extracellular vesicles, wherein a cytokine; linker; and a transmembrane protein are fused in each of the extracellular vesicles, and wherein the drug or physiologically active substance is encapsulated in a lipid layer of the extracellular vesicle.

The cytokine may be IL-2, but it should be noted that the present invention is not limited thereto.

The linker consists of an amino acid sequence represented by the general formula (GGGGS)n (SEQ ID NO: 1), (SGGGG)n (SEQ ID NO: 2), (SRSSG)n (SEQ ID NO: 3), (SGSSC)n (SEQ ID NO: 4), (GKSSGSGSESKS)n (SEQ ID NO: 5), (RPPPPC)n (SEQ ID NO: 6), (SSPPPPC)n (SEQ ID NO: 7), (GSTSGSGKSSEGKG)n (SEQ ID NO: 8), (GST-SGSGKSSEGSGSTKG)n (SEQ ID NO: 9), (GST-SGSGKPGSGEGSTKG)n (SEQ ID NO: 10), or (EGKSSGSGSESKEF)n (SEQ ID NO: 11), wherein n may be an integer from 1 to 20.

The transmembrane domain may be a transmembrane domain of one or more receptors selected from the group consisting of epidermal growth factor receptor, insulin receptor, platelet-derived growth factor (PDGF) receptor, vascular endothelial growth factor receptor, fibroblast growth factor receptor, cholecystokinin (CCK) receptor, neurotrophic factor (NGF) receptor, hepatocyte growth factor (HGF) receptor, Ephrin (Eph) receptor, angiopoietin receptor, and RTK (Related to receptor tyrosine kinase) receptor, but it should be noted that the present invention is not limited thereto.

The drug may be selected from the group consisting of anticancer drugs, anti-inflammatory drugs, antibiotics, antibacterial agents, and vaccines, and the physiologically active material may be selected from the group consisting of peptides, proteins, hormones, and genes, but it should be noted that the present invention is not limited thereto.

MODES FOR CARRYING OUT INVENTION

Hereinafter, the present invention will be described in detail using examples. These examples are merely for illustrating the present invention more specifically, and it would be apparent to those skilled in the art that the scope of the present invention is not limited by these examples.

Example 1: Cell Culture

HEK-293FT cells (human embryonic kidney), B16F10 (mouse melanoma), and B16F10-luc-g5 (mouse melanoma) were cultured in DMEM medium (Hyclone) supplemented with 10% fetal bovine serum and 1% penicillin and streptomycin. Jurkat cells (human T lymphocytes) were cultured in RPMI 1640 medium (Hyclone) supplemented with 10% fetal bovine serum and 1% penicillin and streptomycin. SK-MEL-28 (human melanoma) was cultured in EMEM medium (Hyclone) supplemented with 10% fetal bovine serum and 1% penicillin and streptomycin. CTLL-2 cells (mouse cytotoxic T lymphocytes) were cultured in RPMI-1640 medium supplemented with 10% fetal bovine serum, 1% penicillin and streptomycin, and 20-100 IU/mL of recombinant IL-2 (R&D systems).

Example 2: Lentivirus Preparation

A lentiviral vector containing an antibody-linker-a PDGF receptor transmembrane domain was prepared with reference to the article (Proc Natl Acad Sci USA. 2013 May 14; 110 (20): 8099-104). It was reconstituted and cloned into a lentiviral vector containing the transmembrane domain of the IL-2-linker (GSTSGSGKPGSGEGSTKG (SEQ ID NO: 10))-PDGF receptor.

For transfection, HEK-293FT cells were seeded in a 6-well plate at a density of about $1 \times 10^6$ cells/well, and Lipofectamine 2000 Reagent (ref 11668-027; Thermo fisher scientific), the lentiviral vector expressing the IL-2, and a pCMVD (#PS100001; Origene) and pVSVg (#1733; Addgene) virus packaging vector were mixed in a ratio of 1:1:1 and then incubated overnight at 37° C. in Opti-MEM (ref.31985-070; Gibco) medium. The next day, the supernatant was removed and the medium was replaced with a fresh medium supplemented with 10% fetal bovine serum. At 48 hours thereafter, the supernatant containing the virus was collected, and cell debris was removed using centrifugation and a surfactant-free cellulose acetate (SFCA) membrane filtration device (0.22 μm; Corning). Lentivirus titers were measured using Lenti-X p24 Rapid Titer Kit (#632200; Takara). Lentiviruses were aliquoted and frozen at –80° C.

Example 3: Transduction into Jurkat Cells Using Lentiviruses

Lentivirus expressing 10 μg/mL polybrene and 500 μg/mL IL-2 was added to 0.3 mL RPMI medium, and Jurkat cells ($1\times10^6$ cells/ml) were treated with it. Spinoculation was performed by centrifuging the lentivirus and cell mixture at 30° C. at 1,200×g for 90 minutes. The cells were then incubated overnight at 37° C. with the lentivirus. Excess virus was removed and fresh medium supplemented with 10% fetal bovine serum was added the next day.

Example 4: Analysis of IL-2 Expression in Jurkat Cells Using Real-Time Polymerase Chain Reaction After extracting mRNA (mRNA extraction kit, #9767; TaKaRa) from Jurkat cells transfected with the lentiviral vector, the concentration of mRNA was measured using a nanodrop (DS-11 Series Spectrophotometer; DeNovix). After synthesizing cDNA (SuperScript III First-Strand Synthesis System, Ref. 18080-051; invitrogen) with 100 ng of mRNA, a real-time polymerase chain reaction was performed to analyze the gene expression level of IL-2 (Forward: agacccagggacttaatcag, Reverse: acaatggttgctgtctcatc).

As a result, as shown in FIG. 2(A), it was determined that the gene expression of IL-2 was increased about 1,600 times in Jurkat cells transfected with lentivirus compared to the control group.

Example 5: Analysis of IL-2 Expression in Jurkat Cells Using Flow Cytometry

To determine the expression of IL-2 on the cell surface, Jurkat cells transfected with lentivirus were washed once with phosphate buffered saline (PBS) and fixed with 4% formaldehyde. Thereafter, blocking was performed at 4° C. for 1 hour using PBS supplemented with 1% bovine serum albumin (BSA) and 5% goat serum. Then, after being reacted with anti-Flag antibody (#8146; CST) at 4° C. for 1 hour, they were washed 3 times with PBS, reacted with FITC-conjugated secondary antibody at 4° C. for 1 hour, and washed 3 times with PBS to perform flow cytometry analysis.

As a result, as shown in FIG. 2(B), it was determined that the protein expression of IL-2 on the surface of Jurkat cells transfected with lentivirus was increased by about 46% compared to the control group.

As shown in FIG. 2(C), Jurkat cells transfected with lentivirus were isolated using a flow cytometer.

Example 6: sEV Purification

Control Jukat cells or IL-2 expressing Jukat cells were seeded at a density of about $2\times10^6$ cells/well, and cultured in RPMI medium without fetal bovine serum for 24 hours. Then, in order to isolate sEV or $sEV^{IL-2}$, supernatant obtained from each cell was successively centrifuged at 300×g, 2500×g, and 10,000×g. The supernatant was then filtered through a 0.2 μm syringe filter and centrifuged at 120,000×g. The sEV pellet was resuspended in PBS and centrifuged again at 120,000×g. The purified sEV pellet was resuspended in PBS or 1× cell lysis buffer for the next experiment.

Example 7: IL-2 Expression Analysis of sEV Using ELISA Assay

After $sEV^{IL-2}$ was isolated and purified from the Jurkat cells transfected with lentivirus, an enzyme-linked immunosorbent assay (ELISA) was performed to determine the expression of IL-2 on the surface of sEV. First, an ELISA kit (#550534; BD OptEIA™ Reagent Set B) was used to determine the expression of Flag on the surface of $sEV^{IL-2}$ isolated from the cells. The plate was reacted with an anti-CD63 antibody (ab68418; Abcam) overnight at 4° C. to coat it, and then washed 5 times using a wash buffer. Thereafter, the plate was treated with 5 μg of 4% formaldehyde-fixed $sEV^{IL-2}$ (control group: sEV derived from Naive Jurkat cells) to attach it at room temperature for 1 hour, followed by blocking at room temperature using Assay Diluent for 1 hour. After reaction with anti-Flag antibody (#8146; CST) at room temperature for 1 hour, it was washed 5 times using wash buffer, reacted with HRP-conjugated secondary antibody at room temperature for 1 hour, and then washed 5 times with wash buffer. Finally, after color development for 10 minutes using TMB, color development was stopped using a stop solution. Then, the absorbance was measured at 450 nm using a microplate reader.

In order to determine the expression of IL-2 on the surface of sEV isolated from Jurkat cells transfected with lentivirus by another method, a reproduction experiment was performed using a Human IL-2 Immunoassay (D2050; R& D) kit.

As a result, as shown in FIG. 3, it was determined that the expression of IL-2 was increased on the surface of sEVs derived from Jurkat cells infected with lentivirus compared to the control group.

Example 8: Analysis of Properties of Purified $sEV^{IL-2}$

To determine the properties of purified $sEV^{IL-2}$ using electron microscopy, purified $sEV^{IL-2}$ suspended in PBS was dropped onto formvar carbon-coated nickel grids. After staining with 2% uranyl acetate, the grids were air-dried and the diameter structure was visualized using an HF-3300 (Hitachi) transmission electron microscope.

For immunogold labeling, purified sEV suspended in PBS was placed on formvar carbon-coated nickel grids, and after blocking using PBS supplemented with 0.5% bovine serum albumin, was incubated with a mouse anti-human monoclonal antibody that recognizes Flag. Thereafter, it was incubated with an anti-mouse secondary antibody conjugated with protein A-gold particles (10 nm). It was then washed 5 times with PBS and 10 times with $ddH_2O$ and counterstained with 2% uranyl acetate.

As a result, as shown in FIG. 4, for $sEV^{IL-2}$, it was determined that the protein A-gold particles (10 nm) were labeled by the antibody recognizing Flag.

Example 9: Analysis of sEV Derived from Melanoma Cells Using Nanoparticle Tracking Melanoma cells (B16F10: $5\times10^4$ cell s/ml, SK-MEL-28: $1\times10^5$ cells/ml) were treated with purified $sEV^{IL-2}$ at a concentration of 10 μg/m1 and cultured for 72 hours. Then, the size and concentration of sEV derived from culture supernatant were measured using Nanosight LM10 (Malvern Instruments) equipped with fast video capture and particle tracking software.

As a result, as shown in FIG. 5(A), it was determined by nanoparticle tracking analysis that the number of sEVs decreased in the two types of melanoma cells treated with sEV$^{IL-2}$ compared to the control group.

Example 10: Analysis of sEV Derived from Melanoma Cells Using Western Blot

In order to verify the decrease in the number of the sEVs derived from melanoma cells, the expression level of Rab protein involved in sEV secretion and expression was measured by Western blot. Cytoplasmic or sEV proteins were separated by SDS-PAGE and transferred to a nitrocellulose membrane. Then, the cells were incubated with each primary antibody (ab18211; abcam/Rab5, ab50533; abcam/Rab7, ab55667; abcam/Rab 27a, #4970; Cell signaling/β-actin, ab10931; abcam/PD-L1), and incubated with secondary antibody conjugated with HRP. Images were visualized using enhanced chemiluminescence (ECL) detection reagent (#34095; Thermo Scientific, #RPN2209; GE Healthcare) and quantified using ECL hyperfilm (AGFA, Morstel).

As a result, as shown in FIG. 5(B), it was determined that the protein expression of Rab 27a was significantly reduced in the two types of melanoma cells treated with sEVIL-2 compared to the control group.

In addition, to evaluate the efficacy of sEV$^{IL-2}$ in melanoma, the expression of PD-L1 (programmed death ligand 1) protein, which is known to be the most important for immune evasion of cancer cells, was measured.

As a result, as shown in FIG. 6(A), it was determined that the protein expression of PD-L1 was significantly reduced in the two types of melanoma cells treated with sEV$^{IL-2}$ compared to the control group. This was verified through immunostaining as shown in FIG. 6(B).

Next, Western blot and enzyme-linked immunosorbent assay were performed to evaluate whether exosomal PD-L1 expression from melanoma was regulated by sEV$^{IL-2}$.

As a result, as shown in FIG. 7, it was determined that the expression of exosomal PD-L1 was significantly reduced in melanoma treated with sEV$^{IL-2}$ compared to the control group (A), and it was confirmed by verification using enzyme-linked immunosorbent assay (B).

Example 11: Analysis of Proliferation of Cytotoxic T Cells by sEV$^{IL-2}$

IL-2 is known to be the most important factor in the proliferation and activity of cytotoxic T cells. Therefore, according to the present invention, in order to analyze the effect of sEV$^{IL-2}$ on cytotoxic T cells, cell proliferation analysis was performed using the MTS assay (#G3582; Promega).

CTLL-2 cells were seeded in a 96-well plate at a density of $5\times10^3$ cells/well and cultured for 24 hours. Thereafter, the culture medium was replaced with a fresh medium containing 10% FBS and rIL-2 (100 IU/ml), and control sEV or sEV$^{IL-2}$ (10 μg/ml), and they were further cultured for 24 hours. Then, after adding MTS reagent to each well, carrying out culture at 37° C. for 2 hours, and removing MTS containing the supernatant of each well, absorbance was measured at 490 nm using the microplate reader.

As a result, as shown in FIG. 8, it was determined that the cell proliferation increased about 7 times in CTLL-2 cells treated with sEV$^{IL-2}$ compared to the control group, and it was determined that the response was significantly reduced by the anti-IL-2 antibody.

In other words, from the above results, it was determined that sEV$^{IL-2}$ increased the number of cytotoxic T cells important for cancer cell death, thereby enhancing the immune anticancer efficacy.

Example 12: Analysis of Activity of Cytotoxic T Cells by sEV$^{IL-2}$

Next, in order to confirm expression of Perforin, Granzyme-B (GrzmB), and Interferon-γ (IFN-γ) reported to be involved in the activity of cytotoxic T cells, mRNA was extracted from the control group or cytotoxic T cell treated with sEV$^{IL-2}$ (mRNA extraction kit, #9767; TaKaRa). After measuring the concentration of the extracted mRNA using the nanodrop (DS-11 Series Spectrophotometer; DeNovix), cDNA was synthesized with 100 ng of mRNA (SuperScript III First-Strand Synthesis System, Ref. 18080-051; invitrogen). The gene expression of Perforin (Forward: cgcctacctcaggcttatctc, Reverse: cctcgacagtcaggcagtc), Granzyme-B (Forward:tggggacccagagattaaaa, Reverse: ttttcgtccataggagacaatgc), INF-γ (Forward: tgaccagagcatccaaaaga, Reverse:ctcttcgacctcgaaacagc) was confirmed using the synthesized cDNA by real-time polymerase chain reaction.

As a result, it was determined that the expression of all three genes was significantly increased in the cytotoxic T cells treated with sEV$^{IL-2}$, as shown in FIG. 9(A). In particular, in the case of Interferon-γ, it was determined that the gene expression increased about 9 times compared to the control group.

In other words, from the above results, it was determined that sEV$^{IL-2}$ strongly increased the activity of cytotoxic T cells, which is important for cancer cell death.

It was verified using the flow cytometer as shown in FIG. 9(B). Further, the expression of immune checkpoint PD-1 (programmed cell death-1, Forward:agaatcctggagacctcaac, Reverse:atacccactagggcactcat) was confirmed in the cytotoxic T cells treated with sEV$^{IL-2}$ in the same manner as above.

As a result, as shown in FIG. 10, it was determined that the expressions of PD-1 gene and protein were significantly reduced in the cytotoxic T cells treated with sEV$^{IL-2}$ compared to the control group. This suggests that the anticancer effect can be increased by reducing the immune avoidance due to the binding of cancer cells to PD-L1 due to the decrease in PD-1 of cytotoxic T cells.

Example 13: Co-Culture Assay

In order to prove the anticancer effect by the increase in the activity of cytotoxic T cells along with the decrease in PD-L1 of melanoma cells by sEV$^{IL-2}$, the viability of melanoma cells was determined after co-culture of sEV$^{IL-2}$, melanoma cells (B16F10), and cytotoxic T cells, as shown in FIG. 11(A). Melanoma cells (B16F10-luc-g5) having a cytoluminescent gene were used and analyzed using IVIS spectrum (PerkinElmer).

13-1. Co-culture Assay of Melanoma Cells Pretreated with sEV$^{IL-2}$

Melanoma cells were seeded in a 96-well plate at a density of about $5\times10^3$ cells/well and pretreated with control sEV or sEV$^{IL-2}$ (5 µg/mL). After 24 hours of culture, the cells were cultured with different ratios of CTLL-2 cells (1:1 to 1:10). At the end of culture, MTS reagent was added to each well and they were cultured at 37° C. for 2 hours. After removing MTS containing the supernatant from each well, absorbance was measured at 490 nm using the microplate reader.

13-2. Co-Culture Assay of T Cells Pretreated with sEV$^{IL-2}$

CTLL-2 cells were seeded in a 96-well plate at a density of about $1 \times 10^6$ cells/well and pretreated with control sEV or sEV$^{IL-2}$ (5 µg/mL). After 24 hours of culture, the cells were cultured with different ratios of melanoma cells (1:1 to 1:10). At the end of culture, MTS reagent was added to each well and they were cultured at 37° C. for 2 hours. After removing MTS containing the supernatant from each well, absorbance was measured at 490 nm using the microplate reader.

As a result, as shown in FIGS. 11(B) and (C), it was determined that the viability of melanoma cells was significantly reduced in the co-culture group of cytotoxic T cells and melanoma cells treated with sEV$^{IL-2}$.

Example 14: Cancer Growth Inhibition Assay of sEV$^{IL-2}$ in Melanoma Transplanted Mouse Model $5 \times 10^5$ B16F10 mouse melanoma cells were subcutaneously injected into the right flank of C57BL/6 mice. After 5 days from the start of the experiment, PBS, rhIL-2 (50,000 IU/animal), control sEV or sEV$^{IL-2}$ (20 µg/animal) were directly injected into the cancer tissue 3 times a week. Then, the cancer tissues (long axis*short axis*0.52) of the mice were measured and compared once every 2 days using an engineering digital caliper.

As a result, as shown in FIG. 12(A), cancer growth of the mice injected with sEV$^{IL-2}$ was inhibited more significantly than the PBS control group. Then, weight analysis of the cancer tissues extracted from the mice showed the same result (FIG. 12(B)).

Example 15: Analysis of Blood Exosomal PD-L1 Expression Regulation of sEV$^{IL-2}$ in Melanoma Transplanted Mouse Model After blood was collected from the mice in the above experiment, serum was obtained by centrifugation at 550×g. The supernatant was then centrifuged sequentially at 300×g, 2,500×g, and 10,000×g. Subsequently, the supernatant was filtered through a 0.2 µm syringe filter and centrifuged at 120,000×g. The sEV pellet was resuspended in PBS and centrifuged again at 120,000×g. The purified sEV pellet was cultured with anti-PD-L1 (ab10931; abcam/PD-L1) antibody overnight, and with FITC-conjugated secondary antibody (a11001; invitrogen/goat anti-mouse igg (h+1) cross-adsorbed secondary antibody alexa fluor 488), and analyzed using an sEV flow cytometer (CytoF1EX/Beckman Coulter).

As a result, as shown in FIG. 13(A, B), it was determined that the expression level of exosomal PD-L1 in the mice injected with sEV$^{IL-2}$ was significantly reduced compared to the control group.

Example 16: Cancer Growth Analysis of Melanoma Transplanted Mice according to Co-Treatment with Anticancer Drug $5 \times 10^5$ B16F10 mouse melanoma cells were subcutaneously injected into the right flank of C57BL/6 mice. After 7 days from the start of the experiment, PBS, control sEV (20 µg/animal), sEV$^{IL-2}$ (20 µg/animal), Cisplatin (p4394; Sigma-Aldrich/cis-Diammineplatinum(II) dichloride crystalline), control IgG (be0252; bioxcell/anti-rat IgG2b), and anti-PD-L1 antibody (be0101; bioxcell/anti PD-L1) were injected into the mice twice a week (sEV$^{IL-2}$ or control sEV; intratumoal injection, Cisplatin or PBS; intraperitoneal injection, anti PD-L1 or control IgG; intravenous injection). Thereafter, the cancer tissues (long axis*short axis*0.52) of the mice were measured and compared once every 2 days using the engineering digital caliper.

As a result, as shown in FIG. 14(A, B, C), the cancer growth of mice injected with the anticancer drug together with sEV$^{IL-2}$ was inhibited more significantly than the control group. Then, the weight analysis of the cancer tissues extracted from the mice also showed the same result (FIG. 14(D)).

In addition, as a result of determining the expressions of Rab27a along with PD-L1 in the cancer tissues of melanoma-transplanted mice according to the co-treatment with the anticancer drug by Western blot, it was confirmed that both of PD-L1 and Rab27a in the cancer tissues of mice injected with sEV$^{IL-2}$ showed dramatically reduced expressions as shown in FIG. 15.

The specific parts of the present invention have been described in detail above, and it is clear for those skilled in the art that these specific descriptions are merely preferred embodiments and the scope of the present invention is not limited thereto. Accordingly, the substantial scope of the present invention will be defined by the appended claims and their equivalents.

The scope of the present invention is indicated by the following claims, and all modifications or alternatives derived from the spirit and scope of the claims and their equivalents should be construed as being included in the scope of the present invention.

---

What is claimed is:

1. A method of treating melanoma having increased programmed death ligand 1 (PD-L1) expression, comprising:

administering to a subject a pharmaceutical composition comprising, as an active ingredient, an extracellular vesicle comprising a fusion protein including IL-2, linker, and a transmembrane domain of platelet-derived growth factor (PDGF) receptor, wherein the fusion protein is expressed on a surface of the extracellular vesicle.

2. The method of claim 1, wherein the composition is co-administered with an anticancer drug.

3. A method of treating melanoma having increased programmed death ligand 1 (PD-L1) expression, comprising:

administering to a subject a pharmaceutical composition comprising, as active ingredient, an extracellular vesicle comprising a fusion protein including IL-2, linker, and a transmembrane domain of platelet-derived growth factor (PDGF) receptor, wherein the fusion protein is expressed on a surface of the extracellular vesicle, and cisplatin.

*     *     *     *     *

SEQUENCE LISTING

<160> NUMBER OF SEQ ID NOS: 11

<210> SEQ ID NO 1
<211> LENGTH: 5
<212> TYPE: PRT
<213> ORGANISM: Artificial Sequence
<220> FEATURE:
<223> OTHER INFORMATION: linker

<400> SEQUENCE: 1

Gly Gly Gly Gly Ser

-continued

```
1               5

<210> SEQ ID NO 2
<211> LENGTH: 5
<212> TYPE: PRT
<213> ORGANISM: Artificial Sequence
<220> FEATURE:
<223> OTHER INFORMATION: linker

<400> SEQUENCE: 2

Ser Gly Gly Gly Gly
1               5

<210> SEQ ID NO 3
<211> LENGTH: 5
<212> TYPE: PRT
<213> ORGANISM: Artificial Sequence
<220> FEATURE:
<223> OTHER INFORMATION: linker

<400> SEQUENCE: 3

Ser Arg Ser Ser Gly
1               5

<210> SEQ ID NO 4
<211> LENGTH: 5
<212> TYPE: PRT
<213> ORGANISM: Artificial Sequence
<220> FEATURE:
<223> OTHER INFORMATION: linker

<400> SEQUENCE: 4

Ser Gly Ser Ser Cys
1               5

<210> SEQ ID NO 5
<211> LENGTH: 12
<212> TYPE: PRT
<213> ORGANISM: Artificial Sequence
<220> FEATURE:
<223> OTHER INFORMATION: linker

<400> SEQUENCE: 5

Gly Lys Ser Ser Gly Ser Gly Ser Glu Ser Lys Ser
1               5                   10

<210> SEQ ID NO 6
<211> LENGTH: 6
<212> TYPE: PRT
<213> ORGANISM: Artificial Sequence
<220> FEATURE:
<223> OTHER INFORMATION: linker

<400> SEQUENCE: 6

Arg Pro Pro Pro Pro Cys
1               5

<210> SEQ ID NO 7
<211> LENGTH: 7
<212> TYPE: PRT
<213> ORGANISM: Artificial Sequence
<220> FEATURE:
<223> OTHER INFORMATION: linker

<400> SEQUENCE: 7

Ser Ser Pro Pro Pro Pro Cys
1               5
```

-continued

```
<210> SEQ ID NO 8
<211> LENGTH: 14
<212> TYPE: PRT
<213> ORGANISM: Artificial Sequence
<220> FEATURE:
<223> OTHER INFORMATION: linker

<400> SEQUENCE: 8

Gly Ser Thr Ser Gly Ser Gly Lys Ser Ser Glu Gly Lys Gly
1               5                   10

<210> SEQ ID NO 9
<211> LENGTH: 18
<212> TYPE: PRT
<213> ORGANISM: Artificial Sequence
<220> FEATURE:
<223> OTHER INFORMATION: linker

<400> SEQUENCE: 9

Gly Ser Thr Ser Gly Ser Gly Lys Ser Ser Glu Gly Ser Gly Ser Thr
1               5                   10                  15

Lys Gly

<210> SEQ ID NO 10
<211> LENGTH: 18
<212> TYPE: PRT
<213> ORGANISM: Artificial Sequence
<220> FEATURE:
<223> OTHER INFORMATION: linker

<400> SEQUENCE: 10

Gly Ser Thr Ser Gly Ser Gly Lys Pro Gly Ser Gly Glu Gly Ser Thr
1               5                   10                  15

Lys Gly

<210> SEQ ID NO 11
<211> LENGTH: 14
<212> TYPE: PRT
<213> ORGANISM: Artificial Sequence
<220> FEATURE:
<223> OTHER INFORMATION: linker

<400> SEQUENCE: 11

Glu Gly Lys Ser Ser Gly Ser Gly Ser Glu Ser Lys Glu Phe
1               5                   10
```